United States Patent [19]
Cross et al.

[11] Patent Number: 5,543,419
[45] Date of Patent: Aug. 6, 1996

[54] QUINUCLIDINE ESTERS PROCESS AND INTERMEDIATE FOR THEIR PREPARATION AND PHARMACEUTICAL COMPOSITIONS CONTAINING THEM

[75] Inventors: Peter E. Cross, Canterbury; Alan Stobie, Deal, both of United Kingdom

[73] Assignee: Pfizer Inc, New York, N.Y.

[21] Appl. No.: 204,260

[22] PCT Filed: Sep. 3, 1992

[86] PCT No.: PCT/EP92/02067

§ 371 Date: Jul. 5, 1994

§ 102(e) Date: Jul. 5, 1994

[87] PCT Pub. No.: WO93/06098

PCT Pub. Date: Apr. 1, 1993

[30] Foreign Application Priority Data

Sep. 14, 1991 [GB] United Kingdom ............. 9119705

[51] Int. Cl.$^6$ .................. A61K 31/435; C07D 453/62
[52] U.S. Cl. ........................... 514/305; 546/137
[58] Field of Search ..................... 514/305; 546/137

[56] References Cited

U.S. PATENT DOCUMENTS 4,843,074  6/1989  Rzeszotavski ............. 514/228.2

FOREIGN PATENT DOCUMENTS 0424021  4/1991  European Pat. Off. .

OTHER PUBLICATIONS

Katekar G. F., Thomson R. M. (1972) Aust. J. Chem. 25, 647–53.

Patel S. K., Paterson I. (1983) Tetrahedron Lett. 24(12) 1315–1318.

Hassner A., Naidorf–Meir S. (1989) J. Org. Chem. 54, 4954–4957.

*Primary Examiner*—Alan L. Rotman
*Assistant Examiner*—Evelyn Huang
*Attorney, Agent, or Firm*—Peter C. Richardson; Paul H. Ginsburg; Garth Butterfield

[57] ABSTRACT

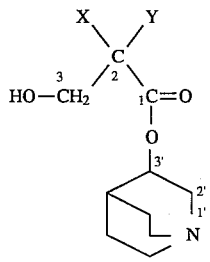

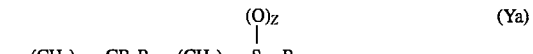

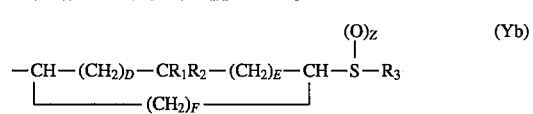

Compounds of formula (I) wherein X is either (a) a phenyl group optionally substituted by 1 or 2 substituents each independently selected from halo, $CF_3$, $C_1$–$C_4$ alkyl, $C_1$–$C_4$ alkoxy and hydroxy or (b) a thienyl group; and Y is of formula (Ya) or (Yb) where A and B are 0, 1 or 2, D and E are 0 or 1, F is 0–3 and D+E+F=1–3, Z is 0, 1 or 2, $R_1$ and $R_2$ are H or alkyl or form a ring, and $R_3$ is $C_1$–$C_4$ alkyl, $C_3$–$C_6$ cycloalkyl or optionally substituted phenyl or benzyl, are antimuscarinic bronchodilators useful for treating chronic obstructive airways disease or asthma.

11 Claims, No Drawings

QUINUCLIDINE ESTERS PROCESS AND INTERMEDIATE FOR THEIR PREPARATION AND PHARMACEUTICAL COMPOSITIONS CONTAINING THEM

This application is the national phase of PCT/EP92/02067 filed on Sep. 3, 1992.

BACKGROUND OF THE INVENTION

This invention relates to 3-quinuclidinyl esters specifically to certain 3-quinuclidinyl 3-hydroxymethyl 2-phenyl or thienyl alkanoates which are lung-selective antimuscarinic bronchodilators. Thus these compounds are particularly useful in the treatment of chronic obstructive airways disease (COAD) and asthma.

COAD is a term encompassing conditions which exhibit, to differing extents, several major progressively developing clinicopathological features, namely inflammatory swelling of airway walls, hypertrophy of submucosal glands, and hyperplasia of epithelial secretory cells leading to hypersecretion of viscous muscous which cannot be cleared effectively, progressive increase in irreversible bronchospasm and decrease in lung function, with respiratory impairment, increasing morbidity and, finally, death.

Thus COAD, and also asthma, are diseases of reduced lung function in which antimuscarinic bronchodilators are known to improve airway patency. However, existing agents are non-selective for smooth muscle muscarinic sites in lung and this reduces their effectiveness as bronchodilators and leads to unwanted side effects. Sub-types of muscarinic receptor are now known to exist in the airways (see P. J. Barnes, P. Minette and J. Maclagan, TIPS, 1988, 9, 412.); M1 receptors are present on sympathetic nerves and parasympathetic ganglia; M2 receptors on pulmonary cholinergic nerves (pre-junctional inhibitory receptors) and M3 receptors are located on smooth muscle (post-junctional receptors). The compounds of the present invention generally have bronchospasmolytic effects at doses which do not significantly affect other tissues such as brain, heart, gastrointestinal tract, eye and salivary gland. Furthermore they generally show selectivity for the lung post-junctional $M_3$ receptors as opposed to the pulmonary. pre-junctional $M_2$ receptors and cardiac $M_2$ receptors. Therapeutic action at some other smooth muscle sites may be envisaged. For example, the compounds are also likely to be useful in treating urinary incontinence.

SUMMARY OF THE INVENTION

The present invention provides a compound of formula (I):

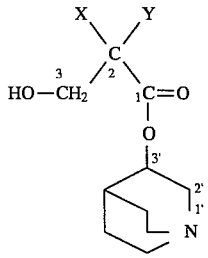

or a pharmaceutically acceptable salt thereof, wherein X is either (a) a phenyl group optionally substituted by 1 or 2 substituents each independently selected from halo, $CF_3$, $C_1$–$C_4$ alkyl, $C_1$–$C_4$ alkoxy and hydroxy or (b) a thienyl group;

and Y is either (a) a group of formula (Ya)

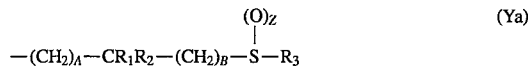

where A and B are independently 0, 1 or 2, or (b) a group of formula (Yb)

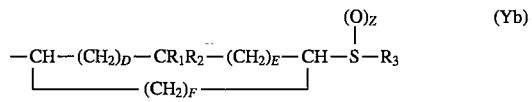

where D and E are independently 0 or 1, F is 0, 1, 2 or 3 and D+E+F=1, 2 or 3,
Z is 0, 1 or 2,
$R_1$ and $R_2$ are independently H or $C_1$–$C_4$ alkyl, or $R_1$ and $R_2$ are joined together to form, with the carbon atom to which they are attached, a 3- to 6- membered carbocyclic ring, and $R^3$ is a $C_1$–$C_4$ alkyl group, a cycloalkyl group or a phenyl or benzyl group optionally substituted by up to 3 substituents each independently selected from halo, $CF_3$, $C_1$–$C_4$ alkyl, $C_1$–$C_4$ alkoxy and hydroxy.

"Halo" means F, Cl, Br or I. $C_3$ and $C_4$ alkyl and alkoxy groups may be straight or branched chain.

X is preferably an unsubstituted phenyl group. When Y is of formula (Ya) $R_1$ and $R_2$ are preferably H or, when A=1 and B=0, $R_1$ and $R_2$ are preferably independently H, methyl or ethyl. $R_3$ is preferably a methyl group.

The compounds of formula (I) have two asymmetric centres, at the positions identified as 2 and 3' in formula (I) above. When $R_1$ and $R_2$ are different the compounds have a third asymmetric centre at the carbon atom to which $R_1$, and $R_2$ are attached, and when Z=1 there is a fourth asymmetric centre at the sulphur atom. All diastereoisomers whether separated or not are within the scope of the invention. The preferred compounds are however the 3R-quinuclidinyl esters. Also the preferred stereochemistry at the 2- position is S when the hydrocarbon moiety of Y adjacent the 2-position has at least two carbon atoms. Thus the preferred compounds are (2S,3'R) 3-quinuclidinyl esters and can be represented as follows:

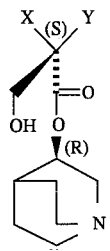

When Z=1 the preferred stereochemistry at the sulphur atom is R, the moiety containing the sulphur atom then being represented as follows:

A particularly preferred individual compound of the invention is (R)-3-quinuclidinyl(2S,Rs)-2-hydroxymethyl-4-(methylsulphinyl)-2-phenylbutanoate.

The compounds of formula (I) in which Z is 0 can be prepared by the reaction of an ester of the formula (II) with a strong base such as lithium or potassium diisopropylamide, potassium t-butoxide or sodium hydride to form a carbanion, followed by reaction of the carbanion with formaldehyde. The formaldehyde is generally provided either as formaldehyde gas, or as paraformaldehyde (which breaks down to formaldehyde in solution).

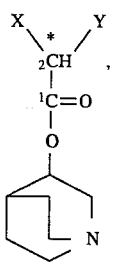
(II)

The preferred techniques are as follows.

In one technique, the ester (II) is reacted for a few hours with lithium diisopropylamide in tetrahydrofuran at about −78° C. The reaction mixture is then slowly allowed to warm to room temperature during which time formaldehyde gas, generated e.g. by heating paraformaldehyde, is intermittently passed into the solution.

In another technique, sodium hydride, the ester (II) and paraformaldehyde are reacted together in dimethylformamide at about room temperature.

Compounds (I) having R stereochemistry at position 3' are preferred, and these are best obtained by starting with an ester (II) having R stereochemistry at position 3' in formula (II). Likewise the 3S quinuclidinyl esters can be prepared from esters (II) having S stereochemistry at the 3'-position.

It is usually most convenient to start with the 2 RS forms of the esters (II) even if the 2R or 2S, rather than 2RS, end products are required. This will result in a mixture of diastereomers of the compounds (I), and, if desired, these can be separated into the 2R and 2S forms by conventional techniques such as chromatography. As stated above, in general, the (2S,3'R) forms of the compounds (I) are preferred when the hydrocarbon moiety of Y has at least two carbon atoms.

The compounds of formula (I) in which Z=1 or 2 may be prepared by oxidation of the corresponding compounds in which Z=0. A suitable oxidising agent is pertrifluoroacetic acid. One method is to add a solution of pertrifluoro acetic acid in trifluoroacetic acid to the compound dissolved in trifluoroacetic acid at a low temperature, such as −10° C., allow the mixture to warm to ambient temperature and evaporate the solution when reaction is complete. The desired compound may be obtained by solvent extraction of the residue. If the sulphonyl compound (Z=2) is desired an excess of pertrifluoroacetic acid may be used, if the sulphinyl compound (Z=1) is to be made the stoichiometric amount of pertrifluoroacetic acid should be used and the temperature kept low. A mixture of Rs and Ss stereoisomers of the sulphinyl compounds is generally obtained and these may be separated by conventional methods such as chromatography.

The starting materials (II) also form part of this invention. They are obtainable by conventional techniques such as the following:

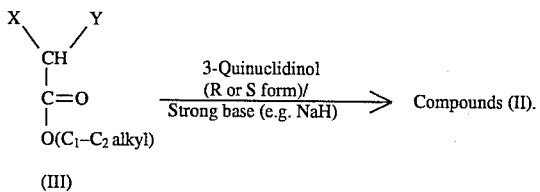

(III)

The reaction is typically carried out by heating the reactants in an organic solvent such as toluene at reflux. The compound (III) is most conveniently used in the RS form, and preferably as the methyl ester.

Alternatively, an acid of formula (IIIA):

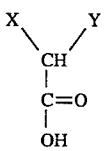
(IIIA)

may be converted to the corresponding acyl halide, for example by reaction with oxalyl chloride in chloroform, and the halide allowed to react with the 3-quinuclidinol to form the compound of formula (II).

In general the materials of formula (III) may be made by reaction of an acid of formula X—CH$_2$—CO$_2$H with a compound of formula Y-Hal, where Hal is chlorine, bromine or iodine, in the presence of a strong base such as lithium di-isopropylamide in an anhydrous solvent such as tetrahydrofuran, followed by acidification, to produce a compound of formula X—CH(CO$_2$H)—Y. This compound may then be converted to the corresponding ester of formula (III) by conventional methods, for example by reaction with methanol or ethanol in the presence of sulphuric acid.

In another method of making compounds of formula (III), a thiol of formula R$_3$—SH reacts with an acid of formula (IV):

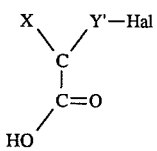
(IV)

where Y' is the hydrocarbon moiety of group Y in formula (I) and Hal is Cl, Br or I, generally in the presence of a strong base such as sodium hydride, followed by esterification.

When Y is a —CH$_2$—S—R$_3$ group the compound of formula (II) may also be prepared by reaction of a compound of formula R$_3$—S—H with a compound of formula (V) in the presence of a strong base:

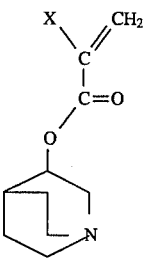
(V)

The compound of formula (II) may then be treated with formaldehyde and a base to yield the compound of formula (I).

The selectivity of the compounds as muscarinic receptor antagonists can be measured as follows.

Male guinea pigs are sacrificed and the ileum, trachea, bladder and right atrium are removed and suspended in Krebs solution under a resting tension of 1 g at 30° C. aerated with 95% O$_2$ and 5% CO$_2$. Contractions of the ileum, bladder and trachea are recorded using an isotonic (ileum) or isometric transducer (bladder and trachea). The frequency of contraction of the spontaneously beating double atria is derived from isometrically recorded contractions.

Dose-response curves to carbachol are determined using a 1–5 minute contact time for each dose to agonist until the maximum response is achieved. The organ bath is drained and refilled with Krebs solution containing the lowest dose of the test compound. The test compound is allowed to equilibrate with the tissue for 20 minutes and the agonist dose-response curve is repeated until the maximum response is obtained. The organ bath is drained and refilled with Krebs solution containing the second concentration of test compound and the above procedure is repeated. Typically three concentrations of the test compound are evaluated on each tissue.

The negative log of the molar concentration ($pA_2$) of the test compound which causes a doubling of the agonist concentration to produce the original response is determined by Schild analysis (Arunlakshana and Schild (1959), Brit. J. Pharmacol., 14, 48–58). Using the above pharmacological techniques, tissue selectivity for muscarinic receptor antagonists is determined.

Activity against agonist-induced or nerve-evoked bronchoconstriction or gut or bladder contractility in comparison with changes in heart rate is determined in the anaesthetised dog, cat or guinea pig. Oral activity is assessed in the conscious dog determining compound effects on lung function, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

The selectivity of the compounds for pulmonary post-junctional as against pre-junctional muscarinic receptors in anaesthetised guinea pigs and cats can be assessed by the following techniques. Acetylcholine released by nerve stimulation activates post-junctional M3 muscarinic receptors to cause contraction of airway smooth muscle and, in addition, activates pre-junctional autoreceptors which inhibit further transmitter release. Animal studies indicate that these pulmonary pre-junctional muscarinic autoreceptors are of the M2 subtype (Barnes et al, 1989). Non-selective agents like ipratropium bromide will inhibit both sites, resulting, in the case of nerve-mediated responses, in an increase in transmitter release which can overcome the post-junctional receptor blockade. Published literature has shown that ipratropium bromide can actually potentiate vagally-induced bronchoconstriction in anaesthetised guinea pigs (Fryer and Maclagan, Eur. Jou. Pharmacol., 139, 187–191 (1987)). Thus, the effects of the test compounds on pre- and post-junctional muscarinic sites can be determined in vivo by comparing the effect on nerve mediated responses with the effect on responses to exogenously adminstered acetylcholine.

For example, the compound of Example 29 has been found to antagonise both acetylcholine-induced, and vagally-induced, bronchoconstriction in anaesthetised guinea pigs over the same dose range. This contrasts with ipratropium bromide which is significantly less potent against vagally-induced than against acetylcholine-induced bronchoconstriction. Additionally, at doses below 1 μg/kg of ipratropium bromide, vagally-induced bronchoconstriction is actually potentiated, confirming its pre-junctional effects.

Similar results were obtained from the compound of Example 29 in the anaesthetised cat. The animals were pretreated with propranolol because high sympathetic tone under chloralose anaesthesia may oppose potentiation of vagus nerve-induced bronchoconstriction. The test results indicate that, in addition to its high potency, the compound of Example 29, in contrast to ipratropium bromide, does not interrupt negative feedback control of transmitter release in both guinea-pig and cat. This confirms the demonstrated in vitro selectivity of this compound for M3 as opposed to M2 muscarinic receptors.

As a result of this selectivity for post- as opposed to pre-junctional muscarinic receptors, the compounds of the invention should be more effective bronchodilators in respiratory disease compared to ipratropium bromide.

The acid addition salts of the compounds of formula (I) can be prepared in a conventional manner by treating a solution or suspension of the free base of (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, ascorbic, benzoic, cinnamic, fumaric, sulphuric, phosphoric, hydrochloric, hydrobromic, hydroiodic, sulfamic, sulfonic such as methanesulfonic, benzenesulfonic, and related acids.

For treatment of the various conditions described above the compounds of formula (I) may be administered to a subject in need of treatment by a variety of conventional routes of administration, including oral administration, and in an aerosol or dry powder composition for administration by inhalation. The compounds have potential for absorption through the gastro-intestinal tract and thus administration by slow release formulations is also possible.

In general, a therapeutically-effective oral dose of the active compounds of formula (I) is likely to range from 0.01 to 1 mg/kg body weight of the subject to be treated, preferably 0.1 to 0.5 mg/kg. In practice the physician will determine the actual dosage which will be most suitable for an individual patient and it will vary with age, weight and response of the particular patient. The above dosages are exemplary of the average case but there can, of course, be individual instances where higher or lower dosages ranges are merited, and such are within the scope of this invention.

Although the compounds of formula (I) can be administered alone, they will generally be administered in admixture with a pharmaceutical carrier selected with regard to the intended route of administration and standard pharmaceutical practice. For example, oral administration may be in the form of tablets containing such excipients as starch or lactose, in capsules either alone or in admixture with excipients, in aerosol or dry powder inhaler form, or in the form of elixirs or suspensions containing flavouring or colouring agents.

In a further aspect the invention provides a pharmaceutical composition comprising a compound Of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament.

The invention further includes the use of a compound of the formula (I), or of a pharmaceutically acceptable salt thereof, for the manufacture of a medicament for the treatment of chronic obstructive airways disease or asthma.

Preparation of compounds according to the invention is illustrated by the following Examples.

EXAMPLE 1

(R)-3-Quinuclidinyl (R and S)-3-hydroxy-2-(methylthiomethyl)-2-phenylpropanoate

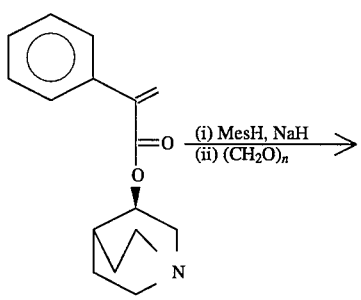

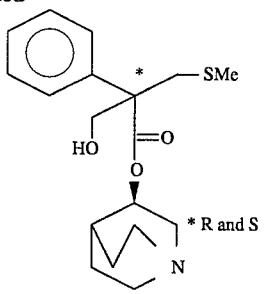

Sodium hydride (2 mg, as an 80% dispersion in oil) was added to a mixture of (R)-3-quinuclidinyl-2-phenylacrylate (see Preparation 1) (1.03 g) and methane thiol (2 ml, of a 10% wt/vol solution in chloroform) in chloroform (8 ml). After 1 hour the mixture was evaporated, and the residue in dimethylformamide (2.5 ml) added to a prestirred (5 min) mixture of paraformaldehyde (240 mg) and sodium hydride (1 mg of an 80% dispersion in oil) in dimethylformamide (10 ml). After 2 hours the mixture was partitioned between ethylacetate and water. The organic layer was washed with water, dried over magnesium sulphate and evaporated to leave a residue that was purified by chromatography on silica gel performing a gradient elution using chloroform plus methanol (0→10%) and ammonia (0→1%) as eluant. Appropriate fractions were combined and evaporated to give the two title compounds, of undefined stereochemistry at C2 as white solids.

Diastereoisomer 1 (higher Rf by tlc) (0.27 g, 40% based on single isomer), m.p. 143°–145° C.

Analysis %: Found: C,64.07; H,7.35; N,4.25; $C_{18}H_{25}NO_3S$ requires: C,64.44; H,7.51; N,4.18.

Diastereoisomer 2 (lower Rf by tlc) (0.17 g, 25% based on single isomer), m.p. 122°–123° C.

Analysis %: Found: C,64.23; H,7.39; N,4.25; $C_{18}H_{25}NO_3S$ requires: C,64.44; H,7.51; N,4.18.

EXAMPLE 2

(R)-3-Quinuclidinyl (R and S)-2-hydroxymethyl-4-(methylthio)-2-phenylbutanoate

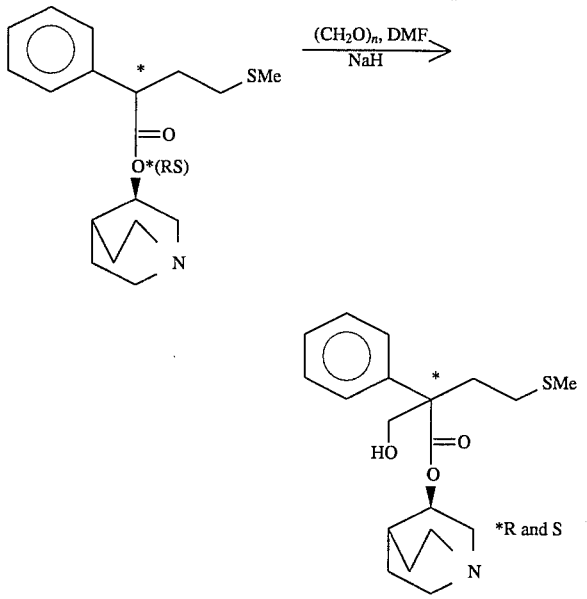

Sodium hydride (3×20 mg portions, as an 80% dispersion in oil) was added over 1 hour to a mixture of (R)-3-quinuclidinyl (RS)-4-(methylthio)-2-phenylbutanoate (see Preparation 2) (22 g) and paraformaldehyde (6.2 g) in dimethylformamide (90 ml) at room temperature. After two hours saturated aqueous ammonium chloride (100 ml) was added at 0° C. and the mixture evaporated. The residue was partitioned between ethylacetate and water, the organic layer dried over magnesium sulphate, and evaporated to give a residue that was purified by chromatography on silica gel performing a gradient elution using chloroform plus methanol (0→10%) and ammonia (0→1%) as eluant. Appropriate fractions were combined and evaporated to give the two title compounds, with the stereochemistry at $C_2$ as indicated, as white solids.

Diastereoisomer 1 (R) stereochemistry (4 g, 33% based on single isomer) m.p. 109°–110° C.

Analysis %: Found: C,65.60; H,7.92; N,4.01; $C_{19}H_{27}NO_3S$ requires: C,65.29; H,7.79; N,4.01.

Diastereoisomer 2 (S) stereochemistry (4.4 g, 37% based on single isomer) m.p. 134°–135° C.

Analysis %: Found: C,65.09; H,7.84; N,3.94; $C_{19}H_{27}NO_3S$ requires: C,65.29; H,7.79; N,4.01.

EXAMPLES 3 TO 10

The following Examples of Table 1 of the general formula:

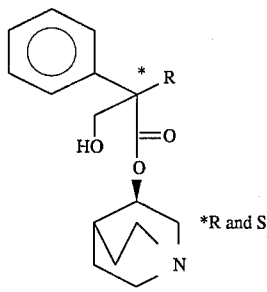

were obtained by similar methods to that described in Example 2 by hydroxymethylation of the appropriately substituted (R)-3-quinuclidinyl esters. Individual experimental variations are indicated in the table. "Diastereoisomers 1 and 2" merely refer to their relative positioning on tlc.

TABLE 1

| Ex. No. | R | Experimental Variations | Analytical Data |
|---|---|---|---|
| 3 | ∠∼C(SMe)(Me) at C₄<br>(see Preparation 3 for starting material) | Reaction quenched by add'n of 2N hydrochloric acid. Chromatography solvent: EtOAC/Et₂O/Et₂NH/MeOH (50:50:5:5:) Each diastereoisomer (at C₂) contains a 50:50 mixture at C₄. | Diastereoisomer 1 - white solid, m.p. 141–143° C.<br>Analysis %: -<br>Found: C, 65.86; H, 8.12; N, 3.86<br>$C_{20}H_{29}NO_3S$ requires: C, 66.08; H, 8.04; N, 3.85.<br>Diastereoisomer 2 - white solid, m.p. 100–102° C.<br>Analysis %: -<br>Found: C, 65.91; H, 7.88; N, 4.00<br>$C_{20}H_{29}NO_3S$ requires: C, 66.08; H, 8.04; N, 3.85. |
| 4 | ∠∼C(SMe)(Et) at C₄<br>(see Preparation 5 for starting material) | Reaction quenched by add'n of 2N hydrochloric acid. Chromatography solvent: EtOAC/Et₂O/Et₂NH/MeOH (50:50:5:5:) Each diastereoisomer (at C₂) contains a 50:50 mixture at C₄. | Diastereoisomer 1 - white solid, m.p. 157–159° C.<br>Analysis %: -<br>Found: C, 66.98; H, 8.41; N, 3.92<br>$C_{21}H_{31}NO_3S$ requires: C, 66.80; H, 8.28; N, 3.71.<br>Diastereoisomer 2 - white solid, m.p. 89–91° C.<br>Analysis %: -<br>Found: C, 66.95; H, 8.01; N, 3.87<br>$C_{21}H_{31}NO_3S$ requires: C, 66.80; H, 8.28; N, 3.71. |
| 5 | ∠∼SPh<br>(see Preparation 6 for starting material) | Dimethylformamide evaporated from reaction without quench. Chromatography solvent: $CHCl_3$ plus MeOH (0→15%) and $NH_3$(aq) (0—1.5%). | Diastereoisomer 1 - white solid, m.p. 105–106° C.<br>Analysis %: -<br>Found: C, 69.76; H, 7.13; N, 3.26<br>$C_{24}H_{29}NO_3S$ requires: C, 70.04; H, 7.10; N, 3.40.<br>Diastereoisomer 2 - white solid, m.p. 138–139° C.<br>Analysis %: -<br>Found: C, 69.77; H, 7.13; N, 3.24<br>$C_{24}H_{29}NO_3S$ requires: C, 70.04; H, 7.10; N, 3.40. |
| 6 | ∠∼S∼<br>(see Preparation 7 for starting material) | Reaction mixture partitioned between water/EtOAC. | Diastereoisomer 1 - white solid, m.p. 114–115° C.<br>Analysis %: -<br>Found: C, 65.98; H, 8.00; N, 3.85<br>$C_{20}H_{29}NO_3S$ requires: C, 66.08; H, 8.04; N, 3.85.<br>Diastereoisomer 2 - white solid, m.p. 140–141° C.<br>Analysis %: -<br>Found: C, 65.22; H, 7.97; N, 3.83<br>$C_{20}H_{29}NO_3S$ requires: C, 66.08; H, 8.04; N, 3.85. |
| 7 | ∠∼S−<<br>(see Preparation 8 for starting material) | Reaction mixture partitioned between water/EtOAC. | Diastereoisomer 1 - white solid, m.p. 137–138° C.<br>Analysis %: -<br>Found: C, 66.57; H, 8.21; N, 3.63<br>$C_{21}H_{31}NO_3S$ requires: C, 66.80; H, 8.28; N, 3.71.<br>Diastereoisomer 2 - white solid, m.p. 153–154° C.<br>Analysis %: -<br>Found: C, 66.58; H, 7.81; N, 3.66<br>$C_{21}H_{31}NO_3S$ requires: C, 66.80; H, 8.28; N, 3.71. |
| 8 | ∠∼∼SMe<br>(see Preparation 9 for starting material) | Reaction mixture partitioned between water/EtOAC. | Diastereoisomer 1 - white solid, m.p. 109–110° C.<br>Analysis %: -<br>Found: C, 66.13; H, 8.01; N, 3.88<br>$C_{20}H_{29}NO_3S$ requires: C, 66.08; H, 8.04; N, 3.85.<br>Diastereoisomer 2 - white solid, m.p. 125–126° C.<br>Analysis %: -<br>Found: C, 66.69; H, 7.97; N, 3.89<br>$C_{20}H_{29}NO_3S$ requires: C, 66.08; H, 8.04; N, 3.85. |
| 9 | ∠∼∼S∼Me<br>(see Preparation 10 for starting material) | Reaction mixture partitioned between water/EtOAC. | Diastereoisomer 1 - white solid, m.p. 109–110° C.<br>Analysis %: -<br>Found: C, 66.49; H, 8.08; N, 3.54<br>$C_{21}H_{31}NO_3S$ requires: C, 66.80; H, 8.28; N, 3.71.<br>Diastereoisomer 2 - white solid, m.p. 117–118° C.<br>Analysis %: -<br>Found: C, 66.57; H, 8.09; N, 3.69<br>$C_{21}H_{31}NO_3S$ requires: C, 66.80; H, 8.28; N, 3.71. |

EXAMPLE 10

(R)-3-Quinuclidinyl (R and S)-2-hydroxymethyl-4-methyl-4-(methylthio)-2-phenylpentanoate

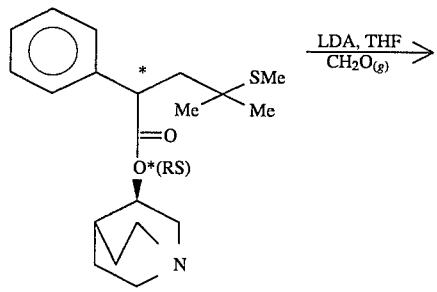

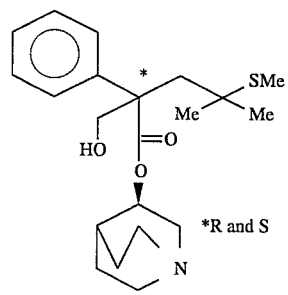

Lithium diisopropylamide (5.7 ml of a 1.5M solution in cyclohexane) was added to a solution of (R)-3quinuclidinyl (RS)-4-methyl-4-(methylthio)-2phenylpentanoate (see Preparation 4) (2.7 g) in tetrahydrofuran (50 ml) at −78° C. After 2 hours the reaction was allowed to slowly reach room temperature during which time formaldehyde gas [generated by heating paraformaldehyde (1.5 g) in a stream of nitrogen] was intermittently added. Saturated ammonium chloride was then added and the product extracted with ethylacetate. The organic layer was dried over magnesium sulphate and evaporated under reduced pressure to give a residue that was purified by chromatography on silica gel using ethylacetate: ether: diethylamine: methanol (50:50:5:5) as eluant. Appropriate fractions were combined and evaporated to give the two title compounds, of undefined stereochemistry at $C_2$ as white solids.

Diastereoisomer 1 (higher Rf by tlc) (0.35 g, 24% based on single isomer) m.p. 179°–180° C.

Analysis %: Found: C,66.56; H,8.37; N,3.49; $C_{21}H_{31}NO_3S$ requires: C,66.80; H,8.28; N,3.71.

Diastereoisomer 2 (lower Rf by tlc) (0.31 g, 21% based on single isomer) m.p. 135°–137° C.

Analysis %: Found: C,66.48; H,8.32; N,3.45; $C_{21}H_{31}NO_3S$ requires: C,66.80; H,8.28; N,3.71.

EXAMPLE 11

(R)-3-Quinuclidinyl (R or S)-3-hydroxy-2-(methylsulphonylmethyl)-2-phenylpropanoate

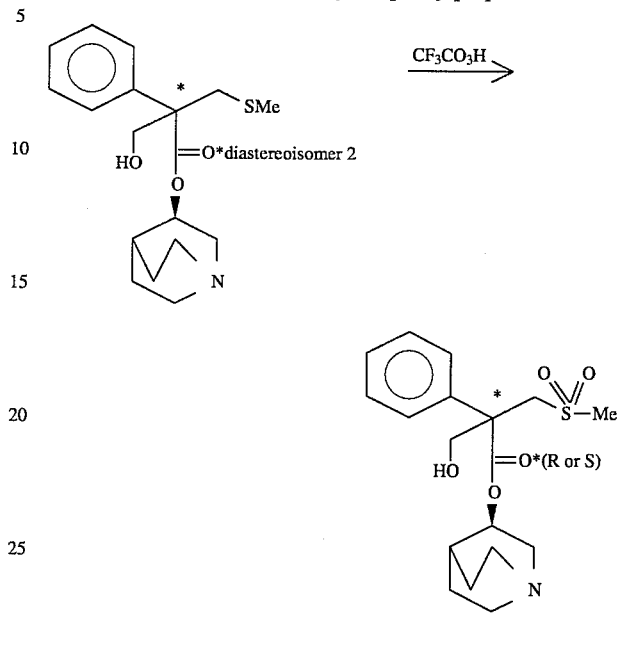

Pertrifluoroacetic acid (0.36 ml of a 3M solution in trifluoroacetic acid) was added to (R)-3-quinuclidinyl (R or S)-3-hydroxy-2-(methylthiomethyl)-2-phenylpropanoate, diastereoisomer 2 (see Example 1), hydrochloride salt (0.2 g) in trifluoroacetic acid (2 ml) at 5° C. The mixture was stirred for ¼ of an hour, warmed to 30° C., stirred for 1 hour and evaporated to give a residue that was partitioned between aqueous 10% potassium carbonate and ethylacetate. The organic layer was dried over sodium sulphate, evaporated, and the residue purified by chromatography on silica gel performing a gradient elution using chloroform plus methanol (0→10%) and aqueous ammonia (0→1%) as eluant. Appropriate fractions were combined and evaporated to give the title compound, a single diastereoisomer of undefined stereochemistry at $C_2$, as a white solid, (90 mg 43%), m.p. 136°–137° C.

Analysis %: Found: C,58.84; H,6.86; N,3.81; $C_{18}H_{25}NO_5S$ requires: C,58.66; H,6.62; N,3.65.

EXAMPLE 12

(R)-3-Quinuclidinyl(S)-2-hydroxymethyl-4-(methylsulphonyl)-2-phenylbutanoate

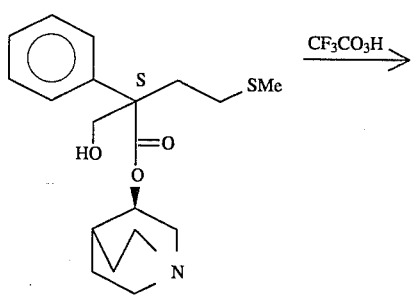

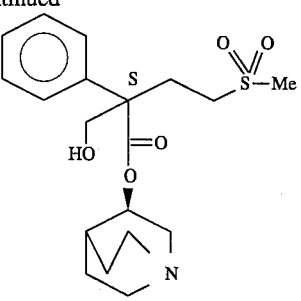

Pertrifluoroacetic acid (0.36 ml of a 3M solution in trifluoroacetic acid) was added to (R)-3-quinuclidinyl (S)-2-hydroxymethyl-4-(methylthio)-2-phenylbutanoate (see Example 2) (0.189 g) in trifluoroacetic acid (2 ml) at −10° C. The mixture was warmed to room temperature, stirred for 1 hour and evaporated. The residue was partitioned between aqueous 10% potassium carbonate and chloroform, the organic layer dried over sodium sulphate and evaporated. The residue was purified by chromatography on silica gel performing a gradient elution using chloroform plus methanol (0→10%) and aqueous ammonia (0→1%) as eluant. Appropriate fractions were combined and evaporated to give the title compound as a white solid, (0.155 g, 74%), m.p. 154°–155° C.

Analysis %: Found: C,59.65; H,7.19; N,3.58; $C_{19}H_{27}NO_5S$ requires: C,59.82; H,7.14; N,3.67.

EXAMPLES 13 TO 20

The following Examples of Table 2 of the general formula:

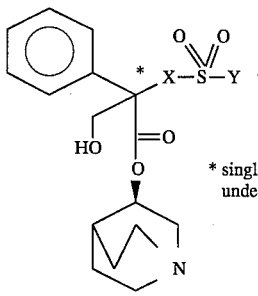

\* single isomer of undefined stereochemistry were obtained by similar methods to that described in Example 12 by oxidation of the appropriate sulphide. The starting sulphides, of undefined stereochemistry at $C_2$, were always the diastereoisomer of lower Rf on tlc described in the appropriate Example. Individual experimental variations are indicated in the table.

TABLE 2

| Ex. No. | X—S—Y | Experimental Variations | Analytical Data |
|---|---|---|---|
| 13 | \*—CH₂—C(C₄)(Me)—SMe (RS) (see Example 3 for starting material) | Aqueous ammonia/ CHCl₃, replaced K₂CO₃/CHCl₃ in initial extractions. Chromatography solvent: EtOAC/Et₂O/ Et₂NH,/MeOH (50:50:5:5). | Yellow oil, as a 50:50 mixture of diastereoisomers at $C_4$. $^1$H-N.M.R. (300 MHz, CDCl₃) δ = 1.0–3.4(m, 20H), 4.1–4.5(m, 2H), 4.9(m, 1H), 7.2–7.3(m, 5H) ppm. Mass Spectrum m/e (MH⁺) = 396. |
| 14 | —CH₂—C(Me)(Me)—SMe (see Example 10 for starting material) | Aqueous ammonia/EtOAC used in initial extraction. No chromatography, product crystallised from ETOAC. | White solid, m.p. 167–169° C. Analysis %: - Found: C, 61.38; H, 7.35; N, 3.25 $C_{21}H_{31}NO_5S$ requires: C, 61.58; H, 7.63; N, 3.42. |
| 15 | —CH₂—C(C₄)(Et)—SMe (see Example 4 for starting material) | Extracted as Example 14. Chromatography as Example 12 to give two partially separated diastereoisomers at $C_4$. | Diastereoisomer 1 (higher Rf on tlc) - white solid, m.p. 144–145° C.. Analysis %: - Found: C, 60.99; H, 7.67; N, 3.30 $C_{21}H_{31}NO_5S.1/4H_2O$ requires: C, 60.92; H, 7.67; N, 3.38. Diastereoisomers 1 & 2 (as a 50:50 mixture) - white solid, m.p. 128–130° C. Analysis \*:- Found: C, 61.57; H, 7.15; N, 3.36 $C_{21}H_{31}NO_5S$ requires: C, 61.58; H, 7.63; N, 3.42. |
| 16 | —CH₂—CH₂—SPh (see Example 5 for starting material) | Chromatography solvent: CHCl₃ plus MeOH (0⎯→15%) and NH₃(aq) (0⎯→1.5%). | White solid, m.p. 179–180° C. Analysis %: - Found: C, 63.67; H, 6.70; N, 3.04 $C_{24}H_{29}NO_5S.1/2H_2O$ requires: C, 63.69; H, 6.68; N, 3.09. |
| 17 | —CH₂—CH₂—SEt (see Example 6 for starting material) | Chromatography solvent: CHCl₃ plus MeOH (0⎯→15%) and NH₃(aq) (0⎯→1.5%). | White solid, m.p. 158–159° C. Analysis %: - Found: C, 57.56; H, 6.88; N, 3.30 $C_{20}H_{29}NO_5S.1/5CHCl_3$ requires: C, 57.85; H, 7.01; N, 3.34. |

TABLE 2-continued

| Ex. No. | X—S—Y | Experimental Variations | Analytical Data |
|---|---|---|---|
| 18 | ⟋⟍⟋S⟨ (see Example 7 for starting material) | Chromatography solvent: CHCl₃ plus MeOH (0—→15%) and NH₃(aq) (0—→1.5%). | White solid, m.p. 187–188° C. Analysis %: - Found: C, 59.68; H, 7.34; N, 3.26 $C_{21}H_{31}NO_5S \cdot 1/8 CHCl_3$ requires: C, 59.77; H, 7.39; N, 3.30. |
| 19 | ⟋⟍⟍SMe (see Example 8 for starting material) | Chromatography solvent: CHCl₃ plus MeOH (0—→15%) and NH₃(aq) (0—→1.5%). | Soild foam, Analysis %: - Found: C, 56.32; H, 6.78; N, 3.16 $C_{20}H_{29}NO_5S \cdot 1/3 CHCl_3$ requires: C, 56.09; H, 6.79; N, 3.20. |
| 20 | ⟋⟍⟍⟍SMe (see Example 9 for starting material) | Chromatography solvent: CHCl₃ plus MeOH (0—→15%) and NH₃(aq) (0—→1.5%). | White solid, m.p. 81–83° C. Analysis %: - Found: C, 61.36; H, 7.29; N, 3.40 $C_{21}H_{31}NO_5S$ requires: C, 61.59; H, 7.63; N, 3.42. |

EXAMPLE 21

(R)-3-Quinuclidinyl (2 R or S, $R_s S_s$)-3-hydroxy-2-(methylsulphinylmethyl)-2-phenylpropanoate

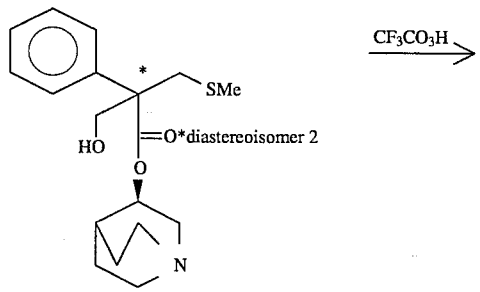

Pertrifluoroacetic acid (0.33 ml of a 3M solution in trifluoroacetic acid) was added to (R)-3-quinuclidinyl (R or S)-3-hydroxy-2-(methylthiomethyl)-2-phenylpropanoate, diastereoisomer 2, (see Example 1) (0.335 g) in trifluoroacetic acid (3 ml) at −5° C. The mixture was stirred for ½ hour, warmed to room temperature, stirred a further 1 hour and evaporated. The residue was partitioned between aqueous 10% potassium carbonate and ethylacetate, the organic layer dried over sodium sulphate and evaporated. The residue was purified by chromatography on silica, performing a gradient elution using chloroform plus methanol (0→10%) and aqueous ammonia (0→1%) as eluant. Appropriate fractions were combined and evaporated to give the title compound a single diastereoisomer of undefined stereochemistry at $C_2$ as a white solid, (0.14 g, 40%), m.p. 126°–127° C.

Analysis %: Found: C,61.49; H,7.24; N,3.79; $C_{18}H_{25}NO_4S$ requires: C,61.51; H,7.17; N,3.99.

EXAMPLES 22 TO 28

The following Examples of Table 3 of the general formula:

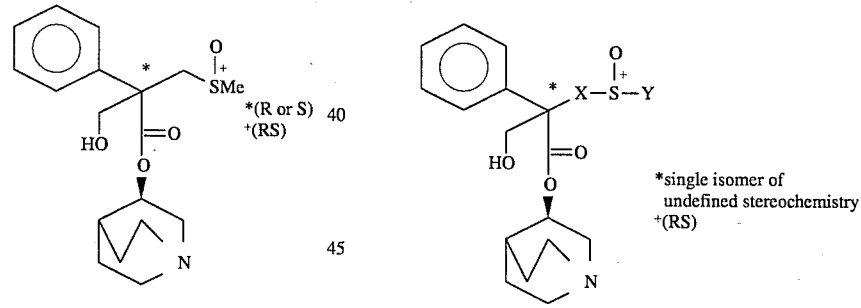

were obtained by similar methods to that described in Example 21 by oxidation of the appropriate sulphide. The starting sulphides, of undefined stereochemistry at $C_2$ were always the second diastereoisomer of lower Rf on tlc described in the appropriate Example. No attempts were made to separate sulphoxide isomers. Individual experimental variations are indicated in the table.

TABLE 3

| Ex. No. | X—S—Y | Experimental Variations | Analytical Data |
|---|---|---|---|
| 22 | ⟋⟍S⟨C₄,Me⟩Me (see Example 3 for starting material) | Aqueous ammonia/ CHCl₃ used for initial extraction. | Yellow viscous oil, as a 50:50 mixture of diastereoisomers at $C_4$. ¹H-N.M.R. (300 MHz, CDCl₃) δ = 1.0–3.4(m, 20H), 4.0–4.5(m, 2H), 4.85(m, 1H), 7.1–7.4(m, 5H) ppm. Mass Spectrum m/e (MH⁺) = 380. |

TABLE 3-continued

| Ex. No. | X—S—Y | Experimental Variations | Analytical Data |
|---|---|---|---|
| 23 | (see Example 10 for starting material) — C(Me)(Me)-S-Me structure | Aqueous ammonia/ EtOAC used for initial extraction. | Viscous clear oil, $^1$H-N.M.R. (300 MHz, CDCl$_3$) $\delta = 0.9$–2.0(m, 11H), 2.2–2.8(m, 10H), 3.1(m, 1H), 4.2–4.5(m, 2H), 4.8(m, 1H), 7.2–7.4(m, 5H) ppm. Mass Spectrum m/e (MH$^+$) = 394. |
| 24 | (see Example 4 for starting material) — CH(Et)-S-Me structure, C$_4$ | Aqueous ammonia/ EtOAC used for initial extraction. | Solid foam, as a 50:50 mixture of diastereoisomers at C$_4$. $^1$H-N.M.R. (300 MHz, CDCl$_3$) $\delta = 0.4$–3.0(m, 22H), 3.3(m, 1H), 4–4.4(m, 2H), 4.9(m, 1H), 5.4–6.0 (BS, 1H), 7.0–7.4(m, 5H) ppm. Mass Spectrum m/e (MH$^+$) = 394. |
| 25 | (see Example 6 for starting material) — SEt | K$_2$CO$_3$/CHCl$_3$, used in extractions. Chromatography solvent: CHCl$_3$ plus MeOH (0——>15%) and NH$_3$(aq) (0——>1.5%). | White solid, m.p. 138–139° C.. Analysis %: - Found: C, 60.14; H, 7.42; N, 3.49 C$_{20}$H$_{29}$NO$_4$S.1/5CHCl$_3$ requires: C, 60.14; H, 7.30; N, 3.47. |
| 26 | (see Example 7 for starting material) — S-CH(Me)$_2$ | K$_2$CO$_3$/CHCl$_3$, used in extractions. Chromatography solvent: CHCl$_3$ plus MeOH (0——>15%) and NH$_3$(aq) (0——>1.5%). | White solid, m.p. 150–151° C.. Analysis %: - Found: C, 63.53; H, 7.50; N, 3.51 C$_{21}$H$_{31}$NO$_4$S requires: C, 64.09; H, 7.94; N, 3.56. |
| 27 | (see Example 8 for starting material) — SMe | K$_2$CO$_3$/CHCl$_3$ used in extractions. Chromatography solvent: CHCl$_3$ plus MeOH (0——>15%) and NH$_3$(aq) (0——>1.5%). | Yellow oil, $^1$H-N.M.R. (300 MHz, CDCl$_3$) $\delta = 1.1$–2.8(m, 19H), 3.1(m, 1H), 4.0(d, 1H), 4.25(d, 1H), 4.85(m, 1H), 7.1–7.5(m, 5H) ppm. Mass Spectrum m/e (MH$^+$) = 380. |
| 28 | (see Example 9 for starting material) — SMe | K$_2$CO$_3$/CHCl$_3$ used in extractions. Chromatography solvent: CHCl$_3$ plus MeOH (0——>15%) and NH$_3$(aq) (0——>1.5%). | Yellow oil, $^1$H-N.M.R. (300 MHz, CDCl$_3$) $\delta = 1.1$–2.9(m, 21H), 3.15(m, 1H), 4.0(d, 1H), 4.2(d, 1H), 4.85(m, 1H), 7.2–7.4(m, 5H) ppm. Mass Spectrum m/e (MH$^+$) = 394. |

EXAMPLE 29

(R)-3-Quinuclidinyl (2S, R$_s$ & S$_s$)-2-hydroxymethyl-4-methylsulphinyl)-2-phenylbutanoate

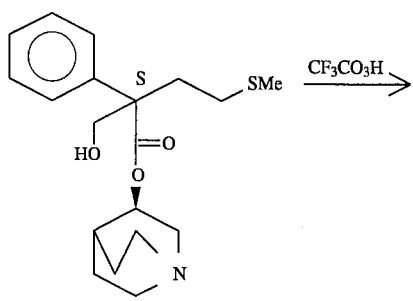

CF$_3$CO$_3$H →

-continued

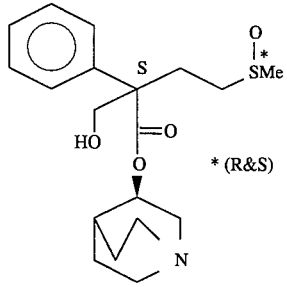

* (R&S)

Pertrifluoroacetic acid (4 ml of a 3M solution in trifluoroacetic acid) was added to (R)-3-quinuclidinyl-(S)- 2-hydroxymethyl-4-(methylthio)-2-phenylbutanoate (see Example 2) (4.19 g) in trifluoroacetic acid (18 ml) at between −3° and 0° C. The mixture was warmed to room temperature, stirred for 1 hour and evaporated. The residue was partitioned between aqueous 10% potassium carbonate and chloroform, the organic layer dried over sodium sulphate and evaporated. The residue was chromatographed on silica, performing a gradient elution using chloroform plus methanol (0→15%) and aqueous ammonia (0→1.5%) as eluant. Appropriate fractions were combined and evaporated to give the title compounds (4 g 91%) as a 50:50 mixture of R$_s$ and S$_s$ diastereoisomers.

This mixture (2×250 mg) was purified by high performance liquid chromatography on Kromasil C-8 silica using water containing trifluoroacetic acid (1%) and acetonitrile (11%) as eluant. Appropriate fractions were combined and evaporated to give the two title compounds with the stereochemistry at sulphur as indicated, as white solids.

Diastereoisomer 1 (first eluted isomer) ($S_s$) stereochemistry (70 mg, 28%, based on single isomer) m.p. 153°–155° C.

Analysis %: Found: C,62.47; H,7.55; N,3.84; $C_{19}H_{27}NO_4S$ requires: C,62.43; H,7.45; N,3.83.

Diastereoisomer 2 (second eluted isomer) ($R_s$) stereochemistry (70 mg, 28%, based on single isomer) m.p. 84°–85° C.

Analysis %: Found: C,62.19; H,7.45; N,3.81; $C_{19}H_{27}NO_4S$ requires: C,62.43; H,7.45; N,3.83.

The following Preparations relate to intermediates for making compounds of the invention.

PREPARATION 1

(R)-3-Quinuclidinyl-2-phenylacrylate

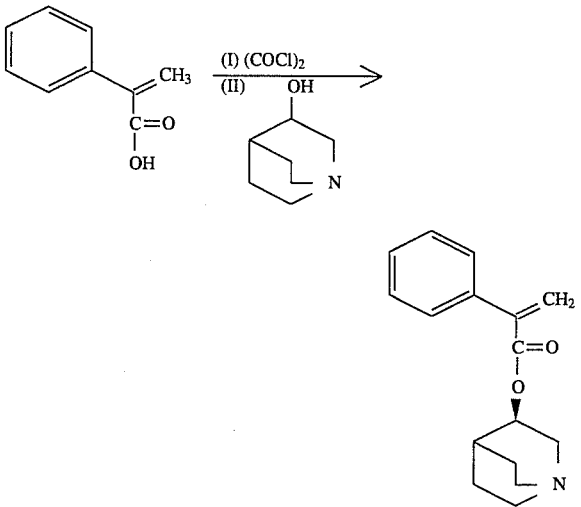

Oxalyl chloride (44.2 ml) was added to a solution of 2-phenylacrylic acid (50 g) (prepared as described in J. Chem. Soc., 2557, 123, 1923) and dimethylformamide (0.5 ml) in chloroform (500 ml). The mixture was stirred for ½ hour, dimethylformamide (0.5 ml) was added and the mixture was stirred for a further ½ hour, then evaporated to give a residue to which chloroform (2×100 ml) was added and evaporated. The residue was finally dissolved in chloroform (500 ml) and to this solution at 10°–15° C. was added (R)-3-quinuclidinol (prepared as described in Acta. Pharm. Suec., 281, 16, 1979) dissolved in chloroform (500 ml). The mixture was stirred for ½ hour, allowed to slowly reach room temperature, evaporated and the residue partitioned between 25% aqueous potassium carbonate and ether. The organic layer was dried over magnesium sulphate, evaporated and the residue recrystallised from hexane to give the title compound, as a white solid, (66 g, 76%) m.p. 83°–85° C.

Analysis %: Found: C,74.39; H,7.47; N,5.45; $C_{16}H_{19}NO_2$ requires: C,74.67; H,7.44; N,5.44.

PREPARATION 2

(R)-3-Quinuclidinyl (RS)-4-(methylthio)-2-phenylbutanoate

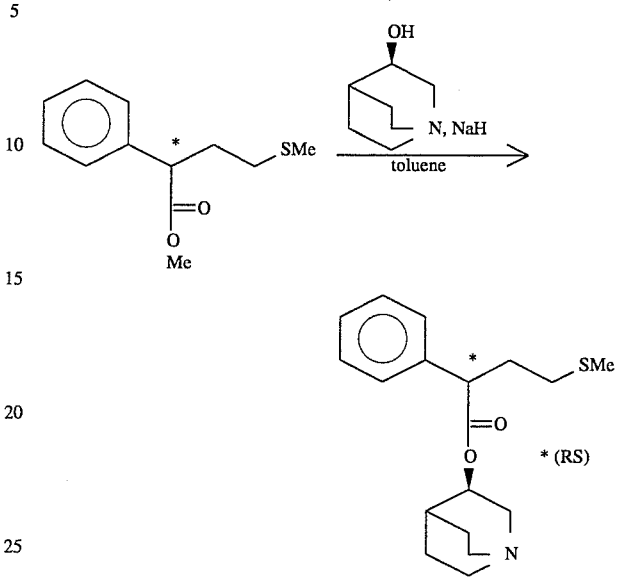

Sodium hydride (0.64 g, as an 80% dispersion in oil) was added to a mixture of methyl-(RS)-4-(methylthio)-2-phenylbutanoate (see Preparation 11) (19.1 g) and (R)-3-quinuclidinol (prepared as described in Acta. Pharm. Suec., 281, 16, 1979) (12.7 g) in toluene (440 ml). The mixture was refluxed with continuous removal of distillate and when necessary replacement with fresh toluene for 1.5 hours. The cooled mixture was extracted with 2M hydrochloric acid, the aqueous layer washed with ethylacetate, basified with potassium carbonate and extracted with chloroform. The organic layer was dried over sodium sulphate, evaporated and the residue partitioned between ethylacetate and aqueous 10% potassium carbonate. The organic layer was dried over sodium sulphate and evaporated to leave the title compound (22.4 g, 82%) as a yellow oil.

$^1$H-N.M.R. (300 MHz, CDCl$_3$) δ=1.1–1.7(m, 6H), 1.8–2.2(m,6H), 2.2–2.8(m,5H), 3.1(m,1H), 3.7(t,1H), 4.7(m,1H), 7.2 (m,5H) ppm.

PREPARATIONS 3 TO 6

The following preparations of Table 4 of the general formula:

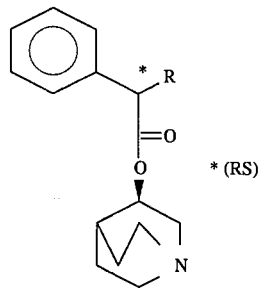

were obtained by similar methods to that described in Preparation 2, by an ester exchange reaction between the appropriately substituted phenylacetic acid methyl ester and R-3-quinuclidinol. Individual experimental variations are indicated in the table, diastereoisomers were not separated.

TABLE 4

| Prep. No. | Ester | Experimental Variations | Analytical Data |
|---|---|---|---|
| 3 | (see Preparation 12 for starting material) | Product purified by chromatography on silica gel using CHCl₃ + MeOH (0→20%) as eluant. | Yellow oil, ¹H-N.M.R. (300 MHz, CDCl₃) $\delta = 1.1–1.8$(m, 7H), 1.8–2.2(m, 4H), 2.2–2.8(m, 8H), 3.1(m, 1H), 3.9(m, 1H), 4.7(m, 1H), 7.3(m, 5H) ppm. |
| 4 | (see Preparation 13 for starting material) | | Yellow oil, ¹H-N.M.R. (300 MHz, CDCl₃) $\delta = 1.2$(m, 6H), 1.3–2.4(m, 10H), 2.5–2.9(m, 5H), 3.1(m, 1H), 3.8(m, 1H), 4.7(m, 1H), 7.1–7.4(m, 5H) ppm. |
| 5 | (see Preparation 14 for starting material) | | Yellow oil, ¹H-N.M.R. (300 MHz, CDCl₃) $\delta = 0.95$(m, 3H), 1.1–2.8(m, 18H), 3.2(m, 1H), 4.0(m, 1H), 4.8(m, 1H), 7.2–7.4(m, 5H) ppm. |
| 6 | (see Preparation 15 for starting material) | Product purified by chromatography on silica gel using CHCl₃ plus MeOH (0→20%) and NH₃(aq) (0→1%) as eluant. | Yellow oil, Analysis %: - Found: C, 72.98; H, 6.87; N, 3.85 $C_{23}H_{27}NO_2S$ requires: C, 72.40; H, 7.13; N, 3.67. |

PREPARATION 7

(R)-3-Quinuclidinyl (RS)-4-(ethylthio)-2-phenylbutanoate

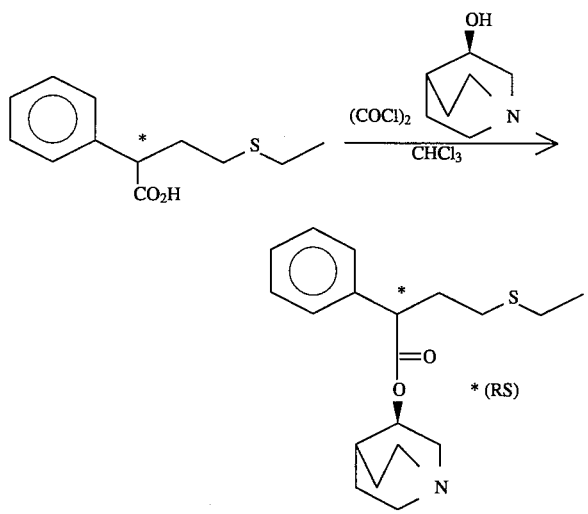

Oxalyl chloride (0.9 ml) in chloroform (2 ml) was added to a solution of (RS)-4-(ethylthio)-2-phenylbutanoic acid (see Preparation 16) (2.0 g) and dimethylformamide (10 μl) in chloroform (20 ml) at room temperature. After 2 hours the mixture was evaporated, and the residue in chloroform (20 ml) treated at 0° C. with (R)-3-quinuclidinol (1.27 g) in chloroform (10 ml). The mixture was allowed to reach room temperature, stirred for 3 hours and then washed with 10% aqueous potassium carbonate. The organic layer was washed with water, dried over sodium sulphate and evaporated to give the title compound (2.3 g, 78%) as a yellow oil.

Analysis %: Found: C,68.24; H,8.06; N,4.48; $C_{19}H_{27}NO_2S$ requires: C,68.63; H,8.19; N,4.21.

PREPARATIONS 8 TO 10

The following preparations of Table 5 of the general formula:

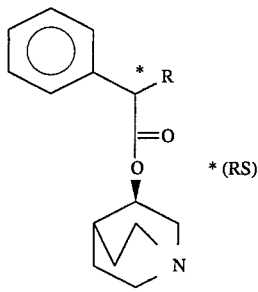

were obtained by similar methods to that described in Preparation 7, by esterification of an appropriately substituted phenylacetic acid with (R)-3-quinuclidinol. Individual experimental variations are indicated in the table, diastereoisomers were separated only in Preparation 8.

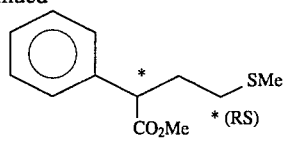

Lithium diisopropylamide (450 ml of a 1.5M solution in cyclohexane) was added to a stirred solution of phenylacetic acid (40.8 g) in tetrahydrofuran (300 ml) at between 0° and 5° C. The mixture was warmed to room temperature, stirred for 1.5 hours, treated with 2-chloroethylmethylsulphide (30 ml) in tetrahydrofuran 30 ml, refluxed for 2 hours, cooled and evaporated. To the residue in methanol (200 ml) was added concentrated sulphuric acid (50 ml) in methanol (250 ml), the mixture refluxed for 1.5 hours, and evaporated. The residue was partitioned between water and chloroform, the organic layer washed with aqueous 10% potassium carbonate, dried over sodium sulphate and evaporated to give a light brown oil (55 g). A portion of this (33 g) was distilled to give the title compound (24.5 g, 61%) as a clear liquid b.p. 128°–135° C. at 5 mm Hg.

$^1$H-N.M.R. (300 MHz, CDCl$_3$) δ=2.0(m,4H), 2.2–2.5(m, 3H), 3.6(s,3H), 3.7(m,1H), 7.1–7.4(m,5H) ppm.

TABLE 5

| Prep. No. | Acid | Experimental Variations | Analytical Data |
|---|---|---|---|
| 8 | (see Preparation 17 for starting material) | Crude product purified by chromatography on silica gel using CHCl$_3$ plus MeOH (0——>10%) and NH$_3$ (aq) (0——>1%) as eluant. The two diastereomers were separated, but recombined for use in Example 16. | Diastereoisomer 1 (higher Rf on tlc) yellow oil. $^1$H-N.M.R. (300 MHz, CDCl$_3$) δ = 1.1–3.0(m, 21H), 3.2(m, 1H), 3.9(t, 1H), 4.85(m, 1H), 7.1–7.5(m, 5H) ppm. Diastereoisomer 2 (lower Rf on tlc) yellow oil. $^1$H-N.M.R. (300 MHz, CDCl$_3$) δ = 1.1–3.0(m, 21H), 3.2(m, 1H), 3.8(t, 1H), 4.85(m, 1H), 7.2–7.5(m, 5H) ppm. |
| 9 | (see Preparation 18 for starting material) | | Yellow oil, $^1$H-N.M.R. (300 MHz, CDCl$_3$) δ = 1.1–1.9(m, 9H), 2.0(s, 3H), 2.0–2.2(m, 2H), 2.2–2.8(m, 5H), 3.1(m, 1H), 3.5(m, 1H), 4.7(m, 1H), 7.0–7.4(m, 5H) ppm. |
| 10 | (see Preparation 19 for starting material) | | Yellow oil, $^1$H-N.M.R. (300 MHz, CDCl$_3$) δ = 1.1–1.9(m, 11H), 1.8–2.2(s, 5H), 2.2–2.9(m, 5H), 3.1(m, 1H), 3.5(t, 1H), 4.8(m, 1H), 7.1–7.5(m, 5H) ppm. |

PREPARATION 11

Methyl (RS)-4-(methylthio)-2-phenylbutanoate

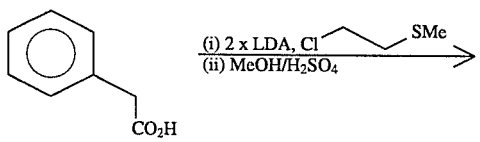

PREPARATIONS 12–15

The following preparations of table 6 of the general formula:

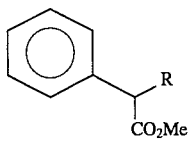

were obtained by similar methods to that described in preparation 7 by alkylation of the di-anion derived from phenylacetic acid with the appropriately substituted chloroethylsulphide (R-Cl). Individual variations are indicated in the table.

PREPARATION 16

(RS)-4-(Ethylthio)-2-phenylbutanoic Acid

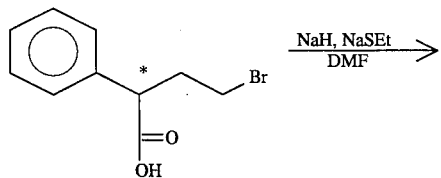

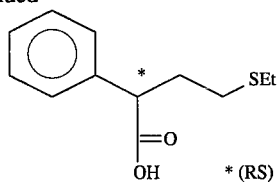

(RS)-4-Bromo-2-phenylbutanoic acid (prepared as described in Farmaco (pavia) Ed. Sci. 355 21(5) 1966) (2.43 g) in dimethylformamide (5 ml) was added to a stirred suspension of sodium hydride (0.33 g, as an 80% dispersion in oil) and ethanethiol sodium salt (1.26 g) in dimethylformamide (15 ml) at 0° C. The mixture was warmed to room temperature, stirred for 2 hours and evaporated. The residue was partitioned between water and ethylacetate, the aqueous layer acidified with concentrated hydrochloric acid and extracted with ethylacetate. The organic layer was dried over sodium sulphate and evaporated to give the title compound (2 g, 89%) as an oil.

Analysis %: Found: C,64.07; H,7.08; $C_{12}H_{16}O_2S$ requires: C,64.25; H,7.19.

TABLE 6

| Prep. No. | R—Cl | Experimental Variations | Analytical Data |
|---|---|---|---|
| 12 | Me–CH(SMe)–Cl (Prepared by the method described in J. Amer. Chem. Soc., 2075, 90, 1968). | The intermediate acid was purified by partitioning evaporated residue between ether/water. The aqueous layer was acidified with 2N HCl and extracted with ether, the ether dried (MgSO₄), evaporated and the residue purified by chromatography on silica gel eluting with dichloromethane. Appropriate fractions were combined, evaporated and the residue esterified. | Yellow oil, $^1$H-N.M.R. (300 MHz, CDCl$_3$) δ = 1.3(m, 3H), 1.8–2.6(m, 6H), 3.65(s, 3H), 3.9(m, 1H), 7.1–7.4(m, 5H) ppm. |
| 13 | Me₂C(SMe)–Cl (Prepared by the method described in J. Amer. Chem. Soc., 2075, 90, 1968). | The intermediate acid was purified by partitioning the evaporated product between 2N HCl and ethylacetate, the organic extracts dried, evaporated and the residue esterified. | Yellow oil, $^1$H-N.M.R. (300 MHz, CDCl$_3$) δ = 1.2(s, 6H), 1.8(m, 1H), 1.95(s, 3H), 2.6(m, 1H), 3.6(s, 3H), 3.9(s, 1H), 7.1–7.4(m, 5H) ppm. |
| 14 | Et–CH(SMe)–Cl (Prepared by the method described in J. Amer. Chem. Soc., 2075, 90, 1968). | The intermediate acid was purified by partitioning evaporated product between ether/water. The aqueous layer was acidified with 2N HCl and extracted with ether, the ether dried (MgSO,), evaporated and the residue purified by chromatography on silica gel eluting with dichloromethane. Appropriate fractions were combined, evaporated and the residue esterified. | Yellow oil, $^1$H-N.M.R. (300 MHz, CDCl$_3$) δ = 1.0(m, 3H), 1.4–2.4(m, 8H), 3.65(d, 3H), 4.0(m, 1H), 7.0–7.3(m, 5H) ppm. |
| 15 | PhS–CH₂CH₂–Cl | The intermediate acid was purified by partitioning the evaporated product between 2N HCl and ethylacetate, the organic extracts dried, evaporated and the residue esterified. | Yellow oil, $^1$H-N.M.R. (300 MHz, CDCl$_3$) δ = 2.1(m, 1H), 2.4(m, 1H), 2.9(m, 2H), 3.7(s, 3H), 3.85(m, 1H), 7.3(m, 10H) ppm. |

PREPARATION 17

(RS)-4-(isopropylthio)-2-phenylbutanoic Acid

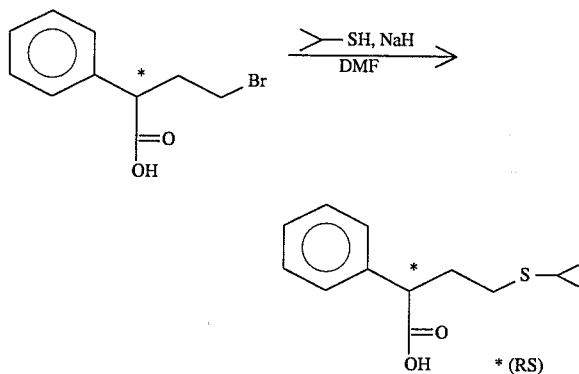

The title compound, as an oil, was prepared by a similar method to that described in Preparation 16 using isopropylthiol sodium salt (generated in-situ from sodium hydride and isopropylthiol) in place of ethanethiol sodium salt.

$^1$H-N.M.R. (300 MHz, CDCl$_3$) δ=1.25(m,6H), 2.1(m, 1H), 2.3–2.5(m,3H), 2.7–3.0(m,2H), 3.8(t,1H), 7.2–7.5(m, 5H) ppm.

PREPARATION 18

(RS)-5-(Methylthio)-2-phenylpentanoic Acid

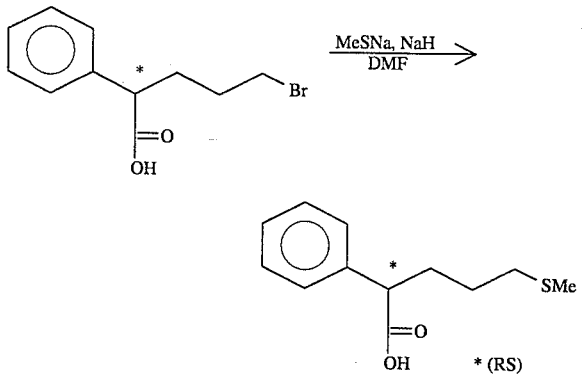

The title compound, as an oil was prepared by a similar method to that described in Preparation 16 using (RS)-5-bromo-2-phenylpentanoic acid (prepared as described in Arkio., For., Kemi., 431, 1957) in place of (RS)-4-bromo-2-phenylpentanoic acid.

$^1$-N.M.R. (300 MHz, CDCl$_3$) δ=1.5(m,2H), 1.8(m, 1H), 2.0(s,3H), 2.1(m, 1H), 2.4(t,2H), 3.5(t,1H), 7.25(s,5H) ppm.

PREPARATION 19

(RS)-6-Methylthio-2-phenylhexanoic Acid

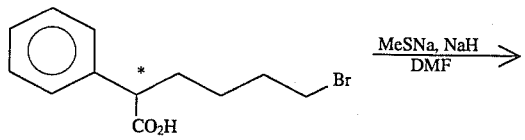

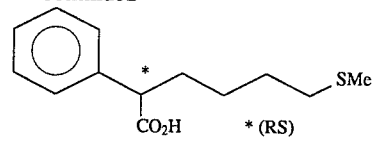

The title compound, as a yellow oil, was prepared by a similar method to that described in Preparation 16 using (RS)-6-bromo-2-phenylhexanoic acid in place of (RS)-bromo-2-phenylbutanoic acid (prepared as described in British Patent No. 1,309,375). $_1$H-N.M.R. (300 MHz, CDCl$_3$) δ=1.3(m,2H), 1.6(m,2H), 1.8(m, 1H), 2.1(m,4H), 2.45(t,2H), 3.55(m, 1H), 7.1–7.5(m,5H) ppm.

We claim:

1. A compound of formula (I):

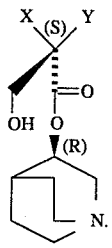

(IA)

or a pharmaceutically acceptable salt thereof, wherein X is either
  (a) a phenyl group optionally substituted by 1 or 2 substituents each independently selected from halo, CF$_3$, C$_1$–C$_4$ alkyl, C$_1$–C$_4$ alkoxy and hydroxy, or
  (b) A thienyl group;

and Y is either (a) a group of formula (Ya)

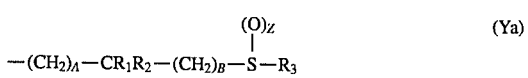

where A and B are independently 0, 1 or 2 or (b) a group of formula (Yb)

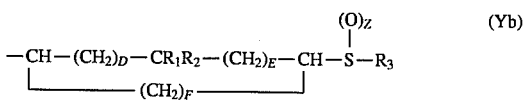

where D and E are independently 0 or 1, F is 0, 1, 2 or 3 and D+E+F=1, 2 or 3;

Z is 0, 1 or 2,

R$_1$ and R$_2$ are independently H or C$_1$–C$_4$ alkyl, or R$_1$ and R$_2$ are joined together to form, with the carbon atom to which they are attached, a 3- or 6-membered saturated or unsaturated carbocyclic ring, and R$_3$ is a C$_1$–C$_4$ alkyl group, a C$_3$–C$_6$ cycloalkyl group or a phenyl or benzyl group optionally substituted by up to 3 substituents each independently selected from halo, CF$_3$, C$_1$–C$_4$ alkyl, C$_1$–C$_4$ alkoxy and hydroxy.

2. A compound according to claim 1, in which X is an unsubstituted phenyl group.

3. A compound according to claim 2, in which Y is of formula (Ya) and R$_1$ and R$_2$ are both H.

4. A compound according to claim 2 in which Y is of formula (Ya), A is 1, B is 0 and R$_1$ and R$_2$ are independently H, methyl or ethyl.

5. A compound according to claim 4, in which R$_3$ is methyl.

6. A compound according to claim 5, of R-stereochemistry at the 3' position and S-stereochemistry at the 2 position having the formula (Ia):

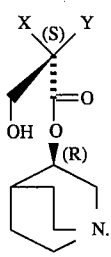

7. A compound according to claim 6, in which Z is 1 and having R-stereochemistry at the sulphur atom of Y, the moiety containing the sulphur atom being of formula:

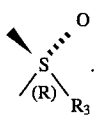

8. (R)-3-Quinuclidinyl (2S,$R_s$)-2-hydroxymethyl-4-(methylsulphinyl)-2-phenylbutanoate.

9. A pharmaceutical composition comprising a compound of formula (I) or (Ia) claim 1, or a pharmaceutically acceptable salt thereof, together with a pharmaceutically acceptable diluent or carrier.

10. A compound of formula (II):

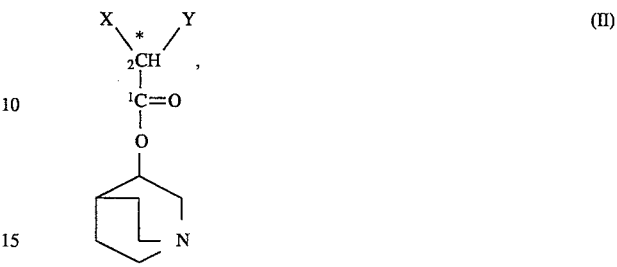

wherein X and Y are as claimed in claim 1.

11. A method of treatment of chronic obstructive airways disease or asthma, which comprises administering to a patient an effective amount of a compound according to claim 1.

* * * * *

UNITED STATES PATENT AND TRADEMARK OFFICE
CERTIFICATE OF CORRECTION

PATENT NO. : 5,543,419

DATED : August 6, 1996

INVENTOR(S) : Peter E. Cross and Alan Stobie

It is certified that error appears in the above-indentified patent and that said Letters Patent is hereby corrected as shown below:

At column 28, lines 17-27 delete

"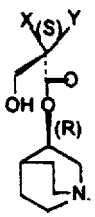 (IA) "

and substitute in place thereof.

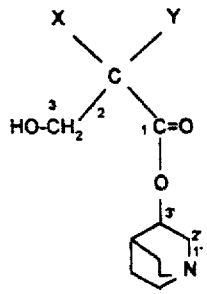 (I)

Signed and Sealed this

Thirteenth Day of May, 1997

Attest:

BRUCE LEHMAN

Attesting Officer    Commissioner of Patents and Trademarks